US012758726B2

(12) United States Patent
Dong et al.

(10) Patent No.: US 12,758,726 B2
(45) Date of Patent: Oct. 13, 2026

(54) ANESTHESIA VENTILATOR DEVICE THAT DYNAMICALLY MONITORS AND REGULATES PARTIAL PRESSURE OF CARBON DIOXIDE

(71) Applicant: Guangzhou Landswick Medical Technologies Ltd., Guangzhou (CN)

(72) Inventors: Hui Dong, Guangzhou (CN); Longchao Zhao, Guangzhou (CN); Caixin Sun, Guangzhou (CN)

(*) Notice: Subject to any disclaimer, the term of this patent is extended or adjusted under 35 U.S.C. 154(b) by 449 days.

(21) Appl. No.: 18/290,448

(22) PCT Filed: Apr. 21, 2023

(86) PCT No.: PCT/CN2023/089765
§ 371 (c)(1),
(2) Date: Nov. 13, 2023

(87) PCT Pub. No.: WO2023/226651
PCT Pub. Date: Nov. 30, 2023

(65) Prior Publication Data

US 2025/0082880 A1 Mar. 13, 2025

(30) Foreign Application Priority Data

May 25, 2022 (CN) ......................... 202210578227.9

(51) Int. Cl.

| | |
|---|---|
| ***A61M 16/01*** | (2006.01) |
| ***A61M 16/00*** | (2006.01) |
| ***A61M 16/10*** | (2006.01) |
| ***A61M 16/20*** | (2006.01) |

(52) U.S. Cl.
CPC ........ *A61M 16/01* (2013.01); *A61M 16/0003* (2014.02); *A61M 16/1075* (2013.01); *A61M 16/208* (2013.01)

(58) Field of Classification Search
CPC .. A61M 16/00; A61M 16/01; A61M 16/0096; A61M 16/0003; A61M 16/1075; A61M 16/10; A61M 16/105; A61M 16/1045; A61M 16/104; A61M 16/12; A61M 16/18; A61M 16/22; A61M 2016/103; A61M 2016/1035; A61M 2202/0007; A61M 2202/02;

(Continued)

(56) References Cited

U.S. PATENT DOCUMENTS 4,611,590 A * 9/1986 Ryschka .............. A61M 16/18 128/203.14
4,903,693 A * 2/1990 Yasue ................ A61M 16/085 600/541

(Continued)

*Primary Examiner* — Colin W Stuart

(57) ABSTRACT

The present invention provides an anesthesia ventilator device that dynamically monitors and regulates the partial pressure of carbon dioxide. The device includes a ventilator main body with inputs connected to an oxygen source, an air source, an anesthetic gas source, and a carbon dioxide source. The output of the ventilator main body is connected to a mask. This invention can solve the technical problem of respiratory alkalosis caused by excessive ventilation in conventional anesthesia ventilator devices, which leads to excessive elimination of carbon dioxide by the patient and a decrease in the partial pressure of carbon dioxide in the body.

9 Claims, 2 Drawing Sheets

(58) Field of Classification Search
CPC .. A61M 2202/0225; A61M 2202/0241; A61M 2202/0283
See application file for complete search history.

(56) References Cited

U.S. PATENT DOCUMENTS

| | | | | | |
|---|---|---|---|---|---|
| 5,049,317 | A * | 9/1991 | Kiske | A61M 16/1015 | 128/203.14 |
| 5,320,093 | A * | 6/1994 | Raemer | A61M 16/085 | 128/914 |
| 5,558,083 | A * | 9/1996 | Bathe | A61M 16/204 | 128/203.14 |
| 5,771,882 | A * | 6/1998 | Psaros | A61M 16/209 | 128/203.14 |
| 6,131,571 | A * | 10/2000 | Lampotang | A61M 16/0069 | 128/204.23 |
| 6,213,120 | B1 * | 4/2001 | Block | A61M 16/0075 | 128/204.23 |
| 2002/0014236 | A1 * | 2/2002 | Dittmann | A61B 5/372 | 128/204.23 |
| 2009/0165785 | A1 * | 7/2009 | Zhang | A61M 16/01 | 128/203.12 |
| 2010/0252046 | A1 * | 10/2010 | Dahlstrom | A61M 16/205 | 128/205.24 |
| 2012/0325208 | A1 * | 12/2012 | Heesch | A61M 16/104 | 128/203.25 |
| 2014/0144439 | A1 * | 5/2014 | Martin | A61M 16/12 | 128/203.14 |
| 2022/0296845 | A1 * | 9/2022 | Jackson | A61M 16/0833 | |

* cited by examiner

ANESTHESIA VENTILATOR DEVICE THAT DYNAMICALLY MONITORS AND REGULATES PARTIAL PRESSURE OF CARBON DIOXIDE

BACKGROUND OF THE PRESENT INVENTION

Field of Invention

The present invention relates to the field of anesthesia technology, particularly to an anesthesia ventilator device that dynamically monitors and regulates partial pressure of carbon dioxide.

Description of Related Arts

An anesthesia ventilator is a device that delivers anesthetic gas to a patient's alveoli using oxygen and air as carriers, forming an anesthetic gas partial pressure. After diffusion into the blood, it directly inhibits the central nervous system, resulting in a general anesthesia effect. Conventional anesthesia ventilators, due to excessive ventilation during use, can cause the patient to exhale too much carbon dioxide, resulting in a decrease in the partial pressure of carbon dioxide in the body and causing respiratory alkalosis (hyperventilation).

SUMMARY OF THE PRESENT INVENTION

The present invention provides an anesthesia ventilator device that dynamically monitors and regulates partial pressure of carbon dioxide to solve the technical problem of respiratory alkalosis caused by excessive ventilation and excessive exhalation of carbon dioxide in conventional anesthesia ventilators during use.

To solve the above technical problem, the present invention discloses an anesthesia ventilator device that dynamically monitors and regulates partial pressure of carbon dioxide, comprising a ventilator main body connected to an oxygen source, an air source, an anesthetic gas source, and a carbon dioxide source at an input end of the ventilator main body, and a mask connected to an output end of the ventilator main body.

Preferably, the ventilator main body comprises:

- a main gas supply pipeline, with an input end of the main gas supply pipeline connected to the air source and an output end of the main gas supply pipeline connected to the mask;
- a gas supply branch, with an input end of the gas supply branch connected to the oxygen source, anesthetic gas source, and carbon dioxide source, and an output end of the gas supply branch connected to the main gas supply pipeline; and
- an exhalation circuit, with one end of the exhalation circuit connected to the mask and the other end away from the mask connected to the gas supply branch.

Preferably, the gas supply branch comprises:

- a first gas supply branch, with an input end of the first gas supply branch connected to the oxygen source, and an output end of the first gas supply branch connected between the first filter and the first check valve of the main gas supply pipeline;
- a second gas supply branch, with an input end of the second gas supply branch connected to the anesthetic gas source, and an output end of the second gas supply branch connected between the first check valve and the second check valve of the main gas supply pipeline; and
- a third gas supply branch, with an input end of the third gas supply branch connected to the carbon dioxide source and an output end of the third gas supply branch connected between the third check valve and the first pressure sensor of the main gas supply pipeline.

Preferably, the main gas supply pipeline is sequentially connected to the air source, a first filter, a first check valve, a second check valve, a third check valve, a first pressure sensor, and a first flow sensor, and the output end of the main gas supply pipeline is connected to the mask.

Preferably, between the first flow sensor and the mask, there is a heated humidifier, and between the second check valve and the third check valve, there is a breath gas generator.

Preferably, the first gas supply branch is sequentially connected to the oxygen source, a second filter, a second pressure sensor, a first flow control valve, and a second flow sensor, and the output end of the first gas supply branch is connected between the first filter and the first check valve;

The second gas supply branch is sequentially connected to the anesthetic gas source, a third filter, a third pressure sensor, a second flow control valve, and a third flow sensor, and the output end of the second gas supply branch is connected between the first check valve and the second check valve.

The third gas supply branch is sequentially connected to the carbon dioxide source, a fourth filter, a fourth pressure sensor, and a third flow control valve, and the output end of the third gas supply branch is connected between the third check valve and the first pressure sensor.

Preferably, one end of the exhalation circuit is connected to the first gas supply branch, and the other end is connected to the mask.

In the direction from the first gas supply branch to the mask, there are sequentially connected a fourth flow control valve, a fifth pressure sensor, and a pressure regulating diaphragm valve.

An output end of the pressure regulating diaphragm valve is connected to the environment.

The fifth pressure sensor and the pressure regulating diaphragm valve are connected by an exhalation circuit, and a throttle valve is provided on the exhalation circuit. An output end of the throttle valve is connected to the environment.

Preferably, the anesthetic gas source is any one of a nitrous oxide source, an ether source, a sevoflurane source, and a desflurane source.

Preferably, the anesthesia ventilator device further comprises:

- an exhalation circuit, wherein one end of the exhalation circuit communicates with the mask, and the other end, away from the mask, communicates with the environment; and
- an exhaled impurity filtration cleaning assembly, wherein the exhaled impurity filtration cleaning assembly is arranged between the mask and the environment on the exhalation circuit;

The exhaled impurity filtration cleaning assembly comprises:

- a recovery filter assembly casing, which is installed on the exhalation circuit;

two symmetrically arranged impurity filter meshes, which are provided inside the recovery filter assembly casing, and installation holes are opened on the impurity filter meshes;

a filter mesh mounting drive, which is arranged in the first mounting cavity. A magnetic compression piston is slidably connected up and down in the first mounting cavity, and the working end of the magnetic compression piston is fixedly connected to a bottom of the first mounting cavity with a first elastic element. A piezoelectric ceramic is fixedly connected to the bottom of the first mounting cavity;

a filter mesh mounting executing component, which is installed in the second mounting cavity; two symmetrically arranged sliding blocks are slidably connected in the second mounting cavity; a second elastic element is fixedly connected between the two sliding blocks; one end of the two sliding blocks, away from the second elastic element, is used to cooperate with the installation holes; an electromagnet is fixedly connected to one end of the two sliding blocks, close to the second elastic element; the electromagnet is electrically connected to the piezoelectric ceramic;

two symmetrically arranged cleaning liquid storage tanks, which contain cleaning liquid. The cleaning liquid storage tanks are connected to a water inlet funnel; and a filter mesh cleaning assembly, which is arranged in the third mounting cavity.

The filter mesh cleaning assembly comprises:

a threaded shaft, which is rotatably connected in the third mounting cavity. The threaded shaft is equipped with a first driving component for driving the threaded shaft to rotate;

a threaded nut, which is threadedly connected to the threaded shaft;

a connecting bracket, which is fixedly connected to the threaded nut;

a water outlet barrel, which is fixedly connected to one end of the connecting bracket, away from the threaded nut. The water outlet barrel is equipped with several water outlet holes;

two symmetrically arranged electric cleaning extensible brushes, which are fixedly connected to both sides of the water outlet barrel;

a compression airbag, which is sleeved on the threaded shaft. The compression airbag contains a third elastic element; wherein the compression airbag is connected to a suction tube, and one end of the suction tube, away from the compression airbag, serves as an inlet and is located inside the cleaning liquid storage tank; an outlet of the compression airbag is connected to the water outlet barrel, and the suction tube is equipped with a one-way valve;

two symmetrically arranged impurity collection holes, which are set inside the recovery filter assembly casing and located directly below the impurity filter meshes; and two symmetrically arranged partitions, which are slidably connected inside the recovery filter assembly casing. The partitions are equipped with a second driving component for driving the partitions to slide up and down.

Preferably, the air source is equipped with a dust supplement assembly, which comprises:

a negative ion emitter fixedly connected inside the air source;

a mounting fixed plate fixedly connected inside the air source;

two symmetrically arranged coil electromagnets fixedly connected inside the mounting fixed plate, wherein the coil electromagnets are equipped with a first power supply component for supplying power to the coil electromagnets;

two symmetrically arranged cleaning plates slidingly connected inside cleaning plate storage grooves of the mounting fixed plate, wherein a plurality of cleaning bristles are fixedly connected on the cleaning plates;

a reset spring fixedly connected between the cleaning plates and the cleaning plate storage grooves;

a strip-shaped electromagnet fixedly connected at a bottom of the cleaning plates, wherein the strip-shaped electromagnet has opposite magnetic polarity to the coil electromagnets, and a second power supply component is provided on the strip-shaped electromagnet for supplying power to the strip-shaped electromagnet;

a flipping component installed in a flipping component mounting cavity of the mounting fixed plate, wherein the flipping component mounting cavity is equipped with two symmetrically arranged guide grooves;

a guide plate slidingly connected inside the guide grooves;

a cylindrical mounting disk key-connected to a connecting rod, wherein the connecting rod is rotatably connected to the guide plate, and a third driving component is provided on the connecting rod for driving the rotation of the connecting rod;

an electrostatic adsorption net connecting rod, wherein the electrostatic adsorption net connecting rod is rotatably connected to the cylindrical mounting disk, a fourth driving component is provided on the electrostatic adsorption net connecting rod for driving the rotation of the electrostatic adsorption net connecting rod, and one end of the electrostatic adsorption net connecting rod, away from the cylindrical mounting disk, is fixedly connected to an electrostatic adsorption net, wherein the electrostatic adsorption net is a positive net;

a negative pressure fan rotatably connected inside a negative pressure chamber of the air source, wherein the negative pressure fan is equipped with a fifth driving component for driving the rotation of the negative pressure fan;

a dust adsorption net fixedly connected inside the negative pressure chamber;

a dust scraping sleeve slidingly connected on the dust adsorption net, wherein the dust scraping sleeve is trumpet-shaped, and a sliding driving component is provided on the dust scraping sleeve for driving the sliding of the dust scraping sleeve along the dust adsorption net;

a sprayer fixedly connected to the air source; and a dust collection trough, wherein the dust collection trough is provided inside the negative pressure chamber.

The technical solution of the present invention will be further described in detail below with reference to the accompanying drawings and embodiments.

Figure 1:
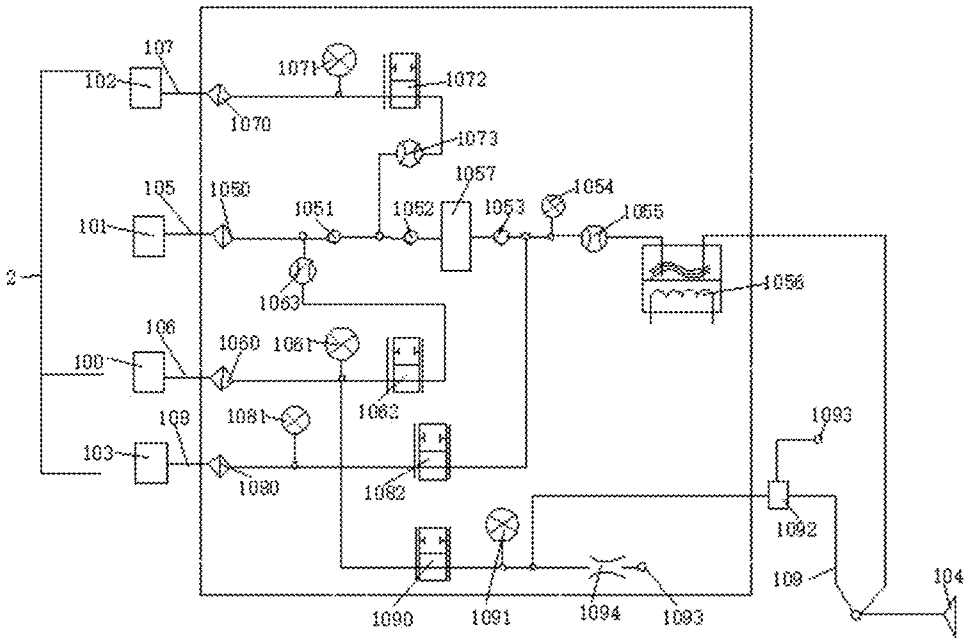
FIG. 1 is a schematic diagram of the ventilator main body system of the present invention.
Figure 2:
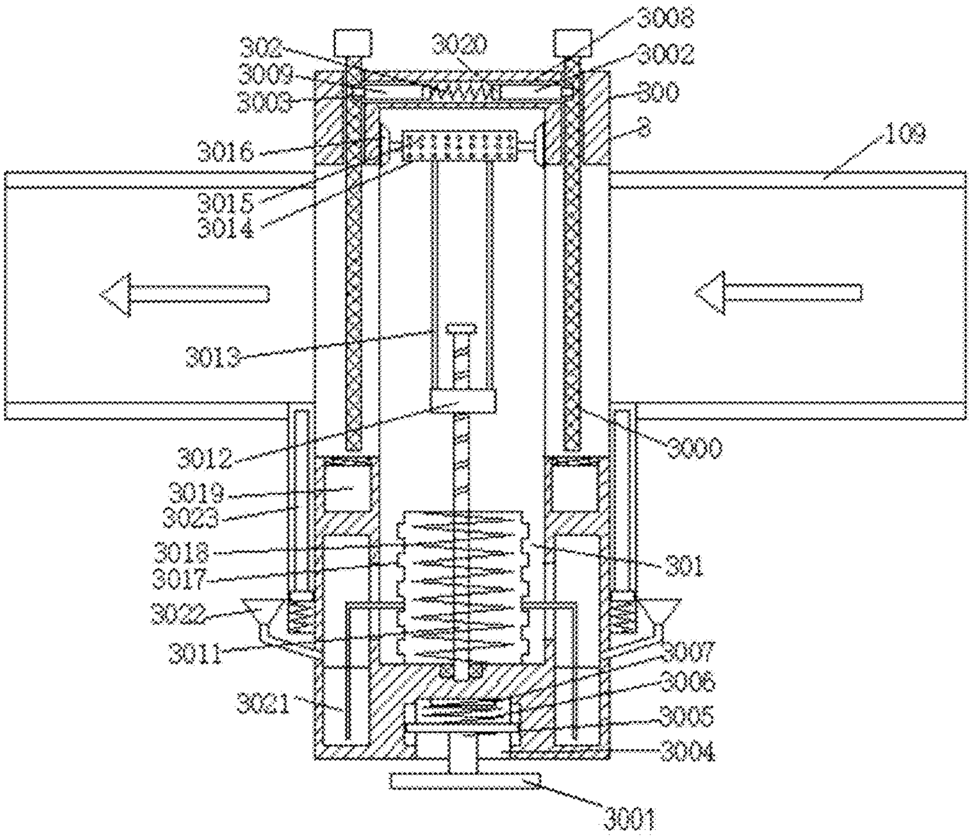
FIG. 2 is a schematic diagram of the structure of the exhaled impurity filtration cleaning assembly of the present invention.
Figure 3:
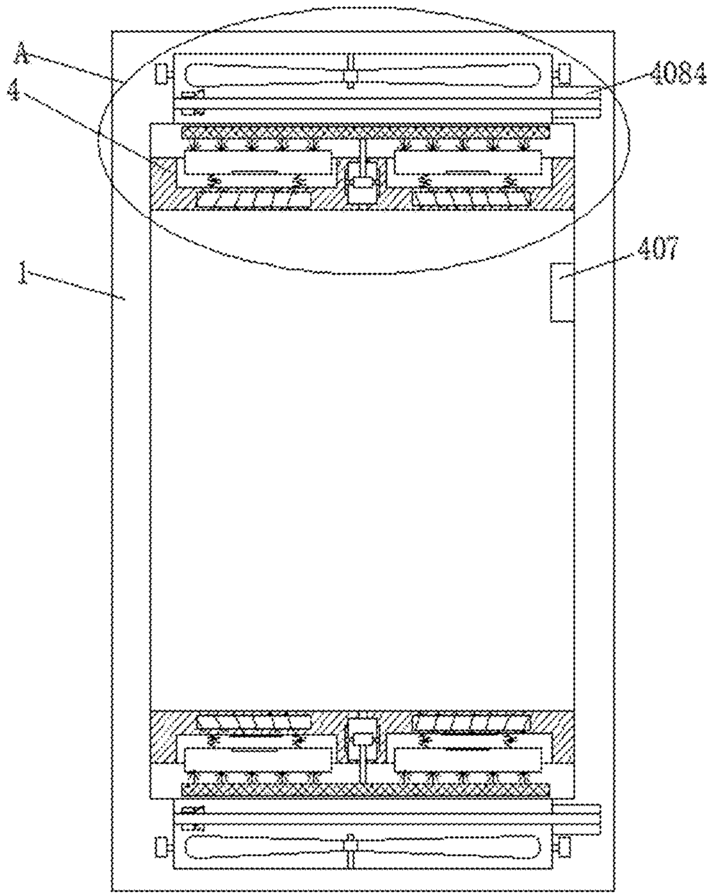
FIG. 3 is a schematic diagram of the structure of the dust supplement assembly of the present invention.

Element reference: 1—Ventilator main body; 100—Oxygen source; 101—Air source; 102—Anesthetic gas source; 103—Carbon dioxide source; 104—Mask; 105—Main gas supply pipeline; 1050—First filter; 1051—First check valve; 1052—Second check valve; 1053—Third check valve; 1054—First pressure sensor; 1055—First flow sensor; 1056—Heated humidifier; 1057—Breath gas generator; 106—First gas supply branch; 1060—Second filter; 1061—Second pressure sensor; 1062—First flow control valve; 1063—Second flow sensor; 107—Second gas supply branch; 1070—Third filter; 1071—Third pressure sensor; 1072—Second flow control valve; 1073—Third flow sensor; 108—Third gas supply branch; 1080—Fourth filter; 1081—Fourth pressure sensor; 1082—Third flow control valve; 109—Exhalation circuit; 1090—Fourth flow control valve; 1091—Fifth pressure sensor; 1092—Pressure regulating diaphragm valve; 1093—Environment; 1094—Throttle valve; 2—Gas supply branch; 3—Exhaled impurity filtration cleaning assembly; 300—Recovery filter assembly casing; 3000—Impurity filter mesh; 3001—Filter mesh mounting drive; 3002—Filter mesh mounting executing component; 3003—Mounting hole; 3004—First mounting cavity; 3005—Magnetic compression piston; 3006—First elastic element; 3007—Piezoelectric ceramic; 3008—Second mounting cavity; 3009—Sliding block; 301—Filter mesh cleaning assembly; 3010—Third mounting cavity; 3011—Threaded shaft; 3012—Threaded nut; 3013—Connecting bracket; 3014—Water outlet barrel; 3015—Water outlet hole; 3016—Electric cleaning extensible brush; 3017—Compression airbag; 3018—Third elastic element; 3019—Impurity collection hole; 302—Second elastic element; 3020—Electromagnet; 3021—Cleaning liquid storage tank; 3022—Water inlet funnel; 3023—Partition; 3024—Suction tube; 4—Dust supplement assembly; 400—Mounting fixed plate; 4000—Cleaning plate storage groove; 401—Coil electromagnet; 402—Cleaning plate; 403—Cleaning bristles; 404—Reset spring; 405—Strip-shaped electromagnet; 406—Flipping component; 4060—Flipping component mounting cavity; 4061—Guide plate; 4062—Guide groove; 4063—Cylinder mounting disk; 4064—Connecting rod; 4065—Electrostatic adsorption net connecting rod; 4066—Electrostatic adsorption net; 407—Negative ion emitter; 408—Negative pressure fan; 4080—Negative pressure chamber; 4081—Dust adsorption net; 4082—Dust scraping sleeve; 4083—Sprayer; 4084—Dust collection trough.

DETAILED DESCRIPTION OF THE PREFERRED EMBODIMENT

The preferred embodiments of the present invention will be described below in conjunction with the accompanying drawings. It should be understood that the preferred embodiments described herein are for the purpose of illustrating and explaining the present invention and are not intended to limit the present invention.

In addition, in the present invention, the terms "first," "second," etc., are used for descriptive purposes only and do not imply any particular order or priority, nor do they limit the present invention. They are merely used to distinguish components or operations described using the same technical terms and should not be construed as indicating or implying the relative importance of the indicated technical features or the quantity of the indicated technical features. Therefore, features designated as "first," "second," etc., may include at least one of such features, either explicitly or implicitly. Furthermore, the technical solutions and technical features of various embodiments can be combined with each other, but such combinations must be based on the ability of ordinary skilled artisans in the field to implement them. When the combination of technical solutions conflicts with each other or cannot be implemented, it should be considered that the combination of such technical solutions does not exist and is not within the scope of protection required by the present invention.

The present invention provides the following embodiments.

Embodiment 1

The present embodiment of the invention provides an anesthesia ventilator device that dynamically monitors and regulates partial pressure of carbon dioxide, as shown in FIGS. 1-4. The device comprises a ventilator main body 1 with an input end connected to an oxygen source 100, an air source 101, an anesthetic gas source 102, and a carbon dioxide source 103, and an output end connected to a mask 104.

Preferably, the anesthetic gas source 102 comprises any one of nitrous oxide gas source, ether gas source, sevoflurane gas source, and desflurane gas source.

The working principle and beneficial effects of the above technical solution are as follows: When in use, the mask 104 is placed on the patient's face, and the oxygen source 100, air source 101, anesthetic gas source 102, and carbon dioxide source 103 are used to provide oxygen, air, anesthetic gas, and carbon dioxide, respectively. Oxygen, air, anesthetic gas, and carbon dioxide are mixed inside the ventilator main body 1 and delivered to the patient's body through the mask 104. Compared to conventional anesthesia ventilator devices, the present invention uses a mixture of oxygen, air source, and carbon dioxide as the carrier gas for delivering anesthetic gas. This can avoid respiratory alkalosis in patients during the use of the anesthesia ventilator device. That is, when the patient eliminates excessive carbon dioxide from the body, the carbon dioxide source 103 can timely replenish the carbon dioxide in the patient's body, thereby preventing a decrease in the partial pressure of carbon dioxide in the patient's body.

The present invention solves the technical problem in conventional anesthesia ventilator devices where excessive ventilation during use can cause the patient to exhale too much carbon dioxide, leading to a decrease in the partial pressure of carbon dioxide in the body and causing respiratory alkalosis.

Embodiment 2

Based on the above the embodiment 1, the ventilator main body 1 comprises:

- a main gas supply pipeline 105, wherein an input end of the main gas supply pipeline 105 is connected to the air source 101, and an output end of the main gas supply pipeline 105 is connected to the mask 104;
- a gas supply branch 2, wherein an input end of the gas supply branch 2 is connected to the oxygen source 100, the anesthetic gas source 102, and the carbon dioxide source 103, and an output end of the gas supply branch 2 is connected to the main gas supply pipeline 105; and an exhalation circuit 109, wherein one end of the exhalation circuit 109 is connected to the mask 104, and the other end, away from the mask 104, is connected to the gas supply branch 2.

The gas supply branch 2 comprises:

a first gas supply branch 106, wherein an input end of the first gas supply branch 106 is connected to the oxygen source 100, and an output end of the first gas supply branch 106 is connected to the main gas supply pipeline 105;

a second gas supply branch 107, wherein an input end of the second gas supply branch 107 is connected to the anesthetic gas source 102, and an output end of the second gas supply branch 107 is connected to the main gas supply pipeline 105; and a third gas supply branch 108, wherein an input end of the third gas supply branch 108 is connected to the carbon dioxide source 103, and an output end of the third gas supply branch 108 is connected to the main gas supply pipeline 105.

On the main gas supply pipeline 105, there are sequentially connected the air source 101, a first filter 1050, a first check valve 1051, a second check valve 1052, a third check valve 1053, a first pressure sensor 1054, and a first flow sensor 1055. The output end of the main gas supply pipeline 105 is connected to the mask 104.

Between the first flow sensor 1055 and the mask 104 on the main gas supply pipeline 105, there is a heated humidifier 1056, and between the second check valve 1052 and the third check valve 1053, there is a breath gas generator 1057.

On the first gas supply branch 106, there are sequentially connected the oxygen source 100, a second filter 1060, a second pressure sensor 1061, a first flow control valve 1062, and a second flow sensor 1063. The output end of the first gas supply branch 106 is connected between the first filter 1050 and the first check valve 1051.

On the second gas supply branch 107, there are sequentially connected the anesthetic gas source 102, a third filter 1070, a third pressure sensor 1071, a second flow control valve 1072, and a third flow sensor 1073. The output end of the second gas supply branch 107 is connected between the first check valve 1051 and the second check valve 1052.

On the third gas supply branch 108, there are sequentially connected the carbon dioxide source 103, a fourth filter 1080, a fourth pressure sensor 1081, and a third flow control valve 1082. The output end of the third gas supply branch 108 is connected between the third check valve 1053 and the first pressure sensor 1054.

One end of the exhalation circuit 109 is connected to the first gas supply branch 106, and the other end is connected to the mask 104. In the direction from the first gas supply branch 106 to the mask 104, there are sequentially connected the fourth flow control valve 1090, fifth pressure sensor 1091, and pressure regulating diaphragm valve 1092.

An output end of the pressure regulating diaphragm valve 1092 is connected to the environment 1093.

Between the fifth pressure sensor 1091 and the pressure regulating diaphragm valve 1092, there is an exhalation branch, and the exhalation branch is equipped with a throttle valve 1094. An output end of the throttle valve 1094 is connected to the environment 1093.

The working principle and beneficial effects of the above technical solution are as follows: During use, air from the air source 101 flows into the main gas supply pipeline 105, oxygen from the oxygen source 100 enters the main gas supply pipeline 105 through the second filter 1060, the second pressure sensor 1061, the first flow control valve 1062, and the second flow sensor 1063. Anesthetic gas from the anesthetic gas source 102 enters the main gas supply pipeline 105 through the third filter 1070, the third pressure sensor 1071, the second flow control valve 1072, and the third flow sensor 1073. Carbon dioxide from the carbon dioxide source 103 enters the main gas supply pipeline 105 through the fourth filter 1080, the fourth pressure sensor 1081, and the third flow control valve 1082. The mixed gas of air, oxygen, anesthetic gas, and carbon dioxide is delivered to the patient for anesthesia through the mask 104 via the main gas supply pipeline 105. The design of the carbon dioxide source 103 prevents the occurrence of excessive ventilation in the patient during the use of the anesthesia ventilator. The exhaled gas from the patient enters the exhalation circuit 109 through the mask 104 and is discharged to the environment 1093 through the pressure regulating diaphragm valve 1092.

The first filter 1050, the second filter 1060, the third filter 1070, and the fourth filter 1080 are used to filter the air from the air source 101 entering the main gas supply pipeline 105, the oxygen from the oxygen source 100 entering the first gas supply branch 106, the anesthetic gas from the anesthetic gas source 102 entering the second gas supply branch 107, and the carbon dioxide from the carbon dioxide source 103 entering the third gas supply branch 108, respectively.

The first pressure sensor 1054, the second pressure sensor 1061, the third pressure sensor 1071, the fourth pressure sensor 1081, and the fifth pressure sensor 1091 are used to detect the pressure in the main gas supply pipeline 105, the first gas supply branch 106, the second gas supply branch 107, the third gas supply branch 108, and the exhalation circuit 109, respectively.

The first flow sensor 1055, the second flow sensor 1063, and the third flow sensor 1073 are used to detect the flow rate of the mixed gas in the main gas supply pipeline 105, the flow rate of oxygen in the first gas supply branch 106, and the flow rate of anesthetic gas in the second gas supply branch 107, respectively.

The first flow control valve 1062, the second flow control valve 1072, and the third flow control valve 1082 are used to regulate and control the flow rate of oxygen in the first gas supply branch 106, the flow rate of anesthetic gas in the second gas supply branch 107, and the flow rate of carbon dioxide in the third gas supply branch 108, respectively.

The first check valve 1051, the second check valve 1052, and the third check valve 1053 prevent backflow of the mixed gas in the main gas supply pipeline 105.

The breath gas generator 1057 is used to generate the mixed input gas, also known as tidal gas, which consists of oxygen, air, and anesthetic gas. The heated humidifier 1056 is used to heat and humidify the tidal gas to make it suitable for patient respiration.

The oxygen from the oxygen source 100 can flow into the environment 1093 through the fourth flow control valve 1090, the fifth pressure sensor 1091, and the throttle valve 1094. By adjusting the fourth flow control valve 1090, the pressure value of the exhalation circuit 109 can be adjusted, which in turn adjusts the detection value of the fifth pressure sensor 1091. Since the fifth pressure sensor 1091 and the pressure regulating diaphragm valve 1092 are in the same circuit, the detection value of the fifth pressure sensor 1091 represents the pressure value (end-expiratory positive pressure) at the pressure regulating diaphragm valve 1092. By adjusting the end-expiratory positive pressure, the respiratory tract can be maintained at a certain positive pressure during the expiration phase, avoiding early closure of the alveoli and promoting the expansion of partially non-ventilated alveoli due to exudation or lung collapse, thereby increasing the functional residual capacity and improving blood oxygenation.

Overall, the described technical solution provides a ventilator system with multiple gas sources (air, oxygen, anesthetic gas, and carbon dioxide) that are filtered, controlled, and mixed to deliver a suitable gas mixture to the patient for anesthesia. It comprises various sensors and valves to monitor and regulate gas pressure and flow rates, ensuring the safety and effectiveness of the respiratory process. Additionally, features such as the carbon dioxide source design and the pressure regulation mechanism contribute to optimizing ventilation and maintaining positive pressure in the respiratory tract.

Embodiment 3

Based on the embodiments 1 or 2, the anesthesia ventilator device further comprises:

- an exhalation circuit 109, wherein one end of the exhalation circuit 109 is in communication with the mask 104, and the other end, away from the mask 104, is in communication with the environment 1093; and
- an exhaled impurity filtration cleaning assembly 3, wherein the exhaled impurity filtration cleaning assembly 3 is arranged between the mask 104 and the environment 1093 on the exhalation circuit 109.

The exhaled impurity filtration cleaning assembly 3 comprises:

- a recovery filter assembly casing 300, which is installed on the exhalation circuit 109;
- two symmetrically arranged impurity filter meshes 3000, which are installed inside the recovery filter assembly casing 300, wherein mounting holes 3003 are provided on the impurity filter meshes 3000;
- a filter mesh mounting drive component 3001, which is arranged in a first mounting cavity 3004, wherein a magnetic compression piston 3005 is slidably connected in the first mounting cavity 3004, and a first elastic element 3006 is fixedly connected between the working end of the magnetic compression piston 3005 and a bottom of the first mounting cavity 3004; a piezoelectric ceramic 3007 is fixedly connected to the bottom of the first mounting cavity 3004;
- a filter mesh mounting executing component 3002, which is installed in a second mounting cavity 3008; wherein two symmetrically arranged sliding blocks 3009 are slidably connected inside the second mounting cavity 3008; a second elastic element 302 is fixedly connected between the two sliding blocks 3009; one end of the sliding blocks 3009, away from the second elastic element 302, is used to cooperate with the mounting holes 3003; an electromagnet 3020 is fixedly connected to an end of the sliding blocks 3009, close to the second elastic element 302, and the electromagnet 3020 is electrically connected to the piezoelectric ceramic 3007;
- two symmetrically arranged cleaning liquid storage tanks 3021, which contain cleaning liquid; wherein an inlet funnel 3022 is connected to the cleaning liquid storage tanks 3021; and
- a filter mesh cleaning assembly 301, which is arranged in a third mounting cavity 3010. The filter mesh cleaning assembly 301 comprises:
  - a threaded shaft 3011, which is rotatably connected in the third mounting cavity 3010; wherein threaded shaft 3011 is equipped with a first driving component for driving the threaded shaft 3011 to rotate;
  - a threaded nut 3012, which is threaded onto the threaded shaft 3011;
  - a connecting bracket 3013, which is fixedly connected to the threaded nut 3012;
  - a water outlet barrel 3014, which is fixedly connected to one end of the connecting bracket 3013, away from the threaded nut 3012, wherein the water outlet barrel 3014 is equipped with several water outlet holes 3015;
  - two symmetrically arranged electric cleaning extensible brushes 3016, which are fixedly connected to both sides of the water outlet barrel 3014;
  - a compression airbag 3017, which is sleeved on the threaded shaft 3011, wherein the compression airbag 3017 contains a third elastic element 3018, the compression airbag 3017 is connected to a suction tube 3024, and one end of the suction tube 3024, away from the compression airbag 3017, serves as an inlet and is located inside the cleaning liquid storage tank 3021; an outlet of the compression airbag 3017 is connected to the water outlet barrel 3014, and a one-way valve is provided inside the suction tube 3024;
  - two symmetrically arranged impurity collection holes 3019, which are located inside the recovery filter assembly casing 300 and directly below the impurity filter meshes 3000; and
  - two symmetrically arranged partitions 3023, which are slidably connected inside the recovery filter assembly casing 300, wherein the partitions 3023 are equipped with a second driving component for driving the partitions 3023 to slide up and down.

The working principle and beneficial effects of the above technical solution are as follows: The exhaled gas from the patient passes through two impurity filter meshes 3000 and is finally discharged into the environment 1093. When the exhaled gas flows through the impurity filter mesh 3000, impurities in the gas adhere to the impurity filter mesh 3000, preventing impurities from blocking the exhalation circuit 109 and ensuring the smooth operation of the anesthesia ventilator.

When replacing the impurity filter mesh 3000, the magnetic compression piston 3005 is manually pressed, causing the magnetic compression piston 3005 to compress the piezoelectric ceramic 3007. After the piezoelectric ceramic 3007 is compressed, the electromagnet 3020 is energized, and the two electromagnets 3020 attract and compress the second elastic element 302. At the same time, the sliding block 3009 transitions from a state of mutual cooperation with the mounting hole 3003 to a state of disengagement from the mounting hole 3003. At this point, the impurity filter mesh 3000 can be manually pulled out for replacement.

Before cleaning the impurity filter mesh 3000, the second driving component is used to drive the partition 3023 to slide upward and close the recovery filter assembly casing 300, preventing cleaning liquid from entering the exhalation circuit 109.

During the cleaning of the impurity filter mesh 3000, the first driving component drives the threaded shaft 3011 to rotate. The rotation of the threaded shaft 3011 moves the threaded nut 3012 along the threaded shaft 3011. When the first driving component drives the threaded shaft 3011 in the forward direction, the threaded nut 3012 moves downward along the threaded shaft 3011. During this downward movement of the threaded nut 3012, the compression airbag 3017 and the third elastic element 3018 are compressed. Then, the first driving component drives the threaded shaft 3011 to reverse, causing the threaded nut 3012 to move upward along the threaded shaft 3011. During this upward movement of the threaded nut 3012, the compression airbag 3017 gradually returns to its original length under the action of the third elastic element 3018. The suction tube 3024 draws water from the cleaning liquid storage tank 3021 into the compressed airbag 3017. When the threaded nut 3012 moves downward again along the threaded shaft 3011, the compression airbag 3017 is compressed again, and the water inside the compression airbag 3017 is pressed into the water outlet barrel 3014 and sprayed out through the water outlet hole 3015. During the movement of the threaded nut 3012, the electric cleaning extensible brush 3016 is driven to move up and down, thereby cleaning the impurity filter mesh 3000. The cleaning intensity of the electric cleaning extensible brush 3016 can be adjusted by extending or retracting it. The cleaned impurities are collected in the impurity collection hole 3019.

Embodiment 4

Based on the embodiment 1, the air source 101 is equipped with a dust supplement assembly 4, which comprises:

- a negative ion emitter 407, fixedly connected inside the air source 101;
- a mounting fixed plate 400, fixedly connected inside the air source 101;
- two symmetrically arranged coil electromagnets 401, fixedly connected inside the mounting fixed plate 400; wherein the coil electromagnets 401 are equipped with a first power supply component for supplying power to the coil electromagnets 401;
- two symmetrically arranged cleaning plates 402, slidingly connected above and below the cleaning plate storage groove 4000 of the mounting fixed plate 400, wherein the cleaning plates 402 are fixedly connected with several cleaning bristles 403;
- a reset spring 404, fixedly connected between the cleaning plates 402 and the cleaning plate storage groove 4000;
- a strip-shaped electromagnet 405, fixedly connected at a bottom of the cleaning plates 402, wherein the strip-shaped electromagnet 405 has opposite magnetic polarity to the coil electromagnets 401 and is equipped with a second power supply component for supplying power to the strip-shaped electromagnet 405;
- a flipping component 406, installed inside the flipping component mounting cavity 4060 of the mounting fixed plate 400, wherein the flipping component mounting cavity 4060 contains two symmetrically arranged guide grooves 4062;
- a guide plate 4061, slidingly connected inside the guide grooves 4062;
- a cylinder mounting disk 4063, key-connected to the connecting rod 4064, wherein the connecting rod 4064 is rotatably connected to the guide plate 4061 and is equipped with a third driving component for driving the rotation of the connecting rod 4064;
- an electrostatic adsorption net connecting rod 4065, rotatably connected to the cylinder mounting disk 4063, wherein the electrostatic adsorption net connecting rod 4065 is equipped with a fourth driving component for driving the rotation of the electrostatic adsorption net connecting rod 4065; one end of the electrostatic adsorption net connecting rod 4065, away from the cylinder mounting disk 4063, is fixedly connected to an electrostatic adsorption net 4066, which is a positively charged net;
- a negative pressure fan 408, rotatably connected inside the negative pressure chamber 4080 of the air source 101 wherein the negative pressure fan 408 is equipped with a fifth driving component for driving the rotation of the negative pressure fan 408;
- a dust adsorption net 4081, fixedly connected inside the negative pressure chamber 4080;
- a dust scraping sleeve 4082, slidingly connected on the dust adsorption net 4081, wherein the dust scraping sleeve 4082 is trumpet-shaped and is equipped with a sliding driving component for driving the sliding motion of the dust scraping sleeve 4082 along the dust adsorption net 4081;
- a sprayer 4083, fixedly connected to the air source 101; and
- a dust collection trough 4084, opened inside the negative pressure chamber 4080.

The working principle and beneficial effects of the above technical solution are as follows: During operation, the negative ion emitter 407 emits negative ions into the air source 101, causing the dust in the air inside the air source 101 to carry a negative charge. Then, the third driving component drives the connecting rod 4064 to rotate. The rotation of the connecting rod 4064 drives the electrostatic adsorption net connecting rod 4065 to flip 180 degrees from the position shown in FIG. 4. Then, power is supplied to the electrostatic adsorption net 4066, and the electrostatic adsorption net 4066 adsorbs the negatively charged dust in the air source 101. The length of the electrostatic adsorption net 4066 can be adjusted by sliding along the guide groove 4062 with the help of the guide plate 4061.

Figure 4:
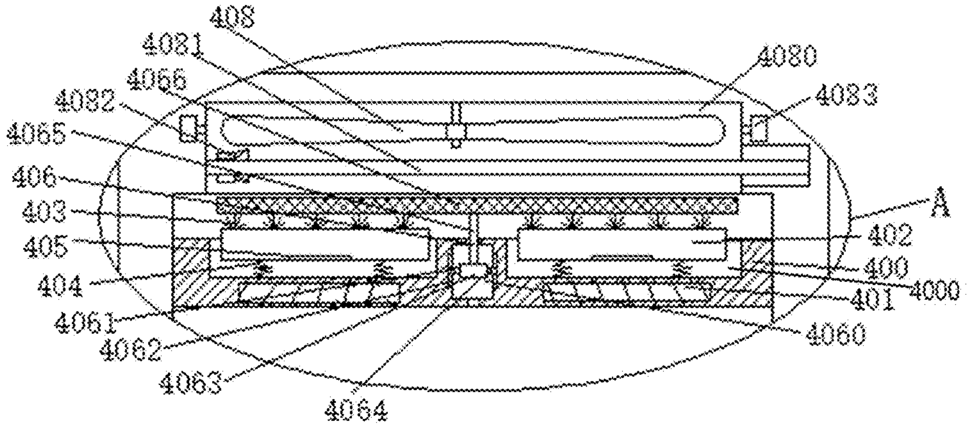
FIG. 4 is a partial enlarged view of location A in FIG. 3 of the present invention.

When cleaning the electrostatic adsorption net 4066, the electrostatic adsorption net 4066 flips back to the position shown in FIG. 4, and the second power supply component is disconnected from the strip-shaped electromagnet 405, while the first power supply component is disconnected from the coil electromagnet 401 (initially, the second power supply component supplies power to the strip-shaped electromagnet 405, and the first power supply component supplies power to the coil electromagnet 401, causing the cleaning plate 402 to be located inside the cleaning plate storage groove 4000 under the action of the electromagnetic force). Under the action of the reset spring 404, the cleaning plate 402 extends out of the cleaning plate storage groove 4000, and the cleaning bristles 403 on it come into contact with the electrostatic adsorption net 4066. At this time, the electrostatic adsorption net 4066 is powered off, and the fourth driving component drives the electrostatic adsorption net connecting rod 4065 to rotate. The rotation of the electrostatic adsorption net connecting rod 4065 drives the electrostatic adsorption net 4066 to rotate, causing the dust on the electrostatic adsorption net 4066 to adhere to the cleaning bristles 403. Then, the electrostatic adsorption net connecting rod 4065 flips again to engage in the adsorption work. Subsequently, the fifth driving component drives the negative pressure fan 408 to rotate, and the negative pressure fan 408 sucks the dust on the cleaning bristles 403 onto the dust adsorption net 4081. Then, the sprayer 4083 wets the dust adsorption net 4081, and the sliding driving component drives the dust scraping sleeve 4082 to slide along the dust adsorption net 4081, scraping the dust on the dust adsorption net 4081 into the dust collection trough 4084.

Embodiment 5

Based on the embodiment 1, the anesthesia ventilator device further comprises:

- an air filter element, wherein the air filter element is arranged inside the air source 101 to filter impurities in the air within the air source; and
- a filter replacement alarm system, wherein the filter replacement alarm system is arranged inside the air source 101 to detect the usage of the air filter element and provide a filter replacement alarm prompt based on the actual usage of the air filter element.

The filter replacement alarm system comprises:

- a first flow rate sensor, wherein the first flow rate sensor is arranged at the intake end of the air filter element inside the air source 101 (the starting end of the airflow direction within the air source 101 to detect the airflow rate on the intake side of the air source 101;
- a second flow rate sensor, wherein the second flow rate sensor is arranged at the outlet end of the air filter element inside the air source 101 (the terminating end of the airflow direction within the air source 101) to detect the airflow rate on the outlet side of the air source 101;
- a timer, wherein the timer is arranged on the air filter element to detect the usage time of the air filter element;
- a controller, and an alarm, wherein the controller is electrically connected to the first flow rate sensor, the second flow rate sensor, the timer, and the alarm. The controller controls the alarm based on the first flow rate sensor, the second flow rate sensor, and the timer, and performs the following steps:

Step 1: calculating the actual blockage condition of the air filter element based on the first flow rate sensor, the second flow rate sensor, and the timer according to the following:

$$\exists = \frac{\frac{\frac{|\mu_1-\mu_2|*\delta*B}{\varphi*\left(\frac{d}{2}\right)^2}*\varepsilon*\gamma_1}{\tau*\Delta P_0*\gamma}}{\sqrt{\frac{\sqrt{d_{max}^2+d_{min}^2}}{d}\lg\left(\omega+\frac{|th-t|}{th}\right)}}$$

wherein $\exists$ is the actual blockage condition of the air filter element, $\mu_1$ is the detection value of the first flow rate sensor, $\mu_2$ is the detection value of the second flow rate sensor, $\delta$ is the dynamic viscosity of the air within the air source 101, B is the thickness of the air filter element, $\varphi$ is the dynamic factor of the air, d is the gap diameter on the air filter element, $\varepsilon$ is the correction factor for the fiber direction of the air filter element, $\gamma$ is the preset capacity density of the air filter element (the amount of impurities per cubic meter of space, in $kg/m^3$), $\gamma_1$ is the preset density of impurities within the air source 101, $\tau$ is the void fraction of the air filter element, $\Delta P_0$ is the baseline pressure difference on both sides of the air filter element when not in use, $\omega$ is the actual usage frequency of the air filter element, t is the detection value of the timer, th is the actual service life of the air filter element, lg is the logarithm with base 10, $d_{max}$ is the maximum preset diameter of impurities in the air, and $d_{min}$ is the minimum preset diameter of impurities in the air; and Step 2: using the controller to compare the actual blockage condition of the air filter element with the preset blockage condition of the air filter element. If the actual blockage condition is greater than the preset blockage condition, the alarm is triggered.

The working principle and beneficial effects of the above technical solution are as follows: Firstly, based on the first flow sensor, the second flow sensor, and a timer, the actual clogging condition of the air filter is calculated. Then, the controller compares the actual clogging condition of the air filter with the preset clogging condition. If the actual clogging condition is greater than the preset condition, the alarm will be triggered. The greater the difference in airflow velocity on both sides of the air filter, the more severe the actual clogging condition. The higher the dynamic viscosity of the air, the more severe the actual clogging condition. The thicker the air filter, the more severe the actual clogging condition. The higher the preset impurity density in the air source 101, the more severe the actual clogging condition of the air filter. The smaller the void ratio of the air filter, the more severe the actual clogging condition. The smaller the preset bulk density of the air filter, the more severe the actual clogging condition. The higher the actual frequency of use of the air filter, the more severe the actual clogging condition. The greater the difference between the actual total usage time and the actual lifespan of the air filter, the more severe the actual clogging condition. The design of the filter replacement alarm system ensures timely replacement of the air filter, guarantees the cleanliness of the air in the oxygen source 101, and improves the safety of the anesthesia ventilator.

Obviously, those skilled in the art can make various modifications and variations to the present invention without departing from the spirit and scope of the invention. Therefore, if these modifications and variations fall within the scope of the claims and equivalent technologies of the present invention, the present invention also intends to include these modifications and variations.

What is claimed is:

1. An anesthesia ventilator device that dynamically monitors and regulates partial pressure of carbon dioxide, comprising a ventilator main body (1) connected to an oxygen source (100), an air source (101), an anesthetic gas source (102), and a carbon dioxide source (103) at an input end of the ventilator main body (1), and connected to a mask (104) at an output end of the ventilator main body (1);

- the air source (101) is equipped with a dust supplement assembly (4), and the dust supplement assembly (4) comprises:
- a negative ion emitter (407), which is fixedly connected inside the air source (101);
- a mounting fixed plate (400), which is fixedly connected inside the air source (101);
- two symmetrically arranged coil electromagnets (401), which are fixedly connected inside the mounting fixed plate (400);
- two symmetrically arranged cleaning plates (402), which are slidingly connected inside a cleaning plate storage groove (4000) of the mounting fixed plate (400); wherein the cleaning plates (402) are fixedly connected with several cleaning bristles (403);
- a reset spring (404), which is fixedly connected between each of the cleaning plates (402) and the cleaning plate storage groove (4000);
- a strip-shaped electromagnet (405), which is fixedly connected at a bottom of each of the cleaning plates (402); wherein the strip-shaped electromagnet (405) has an opposite magnetic polarity to the coil electromagnets (401);
- a flipping component (406), which is installed in a flipping component mounting cavity (4060) of the mounting fixed plate (400); wherein the flipping component mounting cavity (4060) is equipped with two symmetrically arranged guide grooves (4062);
- a guide plate (4061), which is slidingly connected inside the guide grooves (4062);

a cylindrical mounting disk (4063), which is key-connected to a connecting rod (4064); wherein the connecting rod (4064) is rotatably connected to the guide plate (4061);

an electrostatic adsorption net connecting rod (4065), which is rotatably connected to the cylindrical mounting disk (4063); wherein one end of the electrostatic adsorption net connecting rod (4065), away from the cylindrical mounting disk (4063), is fixedly connected to an electrostatic adsorption net (4066), which is a positively charged net;

a negative pressure fan (408), which is rotatably connected inside a negative pressure chamber (4080) of the air source (101);

a dust adsorption net (4081), which is fixedly connected inside the negative pressure chamber (4080);

a dust scraping sleeve (4082), which is slidingly connected to the dust adsorption net (4081); wherein the dust scraping sleeve (4082) is trumpet-shaped;

a sprayer (4083), which is fixedly connected to the air source (101); and a dust collection trough (4084), which is provided inside the negative pressure chamber (4080).

2. The anesthesia ventilator device, as recited in claim 1, wherein the ventilator main body (1) comprises:

a main gas supply pipeline (105), wherein an input end of the main gas supply pipeline (105) is connected to the air source (101), and an output end of the main gas supply pipeline (105) is connected to the mask (104);

a gas supply branch (2), wherein an input end of the gas supply branch (2) is connected to the oxygen source (100), the anesthetic gas source (102), and the carbon dioxide source (103), and an output end of the gas supply branch (2) is connected to the main gas supply pipeline (105); and an exhalation circuit (109), wherein one end of the exhalation circuit (109) is connected to the mask (104), and the other end, away from the mask (104), is connected to the gas supply branch (2).

3. The anesthesia ventilator device, as recited in claim 2, wherein the gas supply branch (2) comprises:

a first gas supply branch (106), wherein an input end of the first gas supply branch (106) is connected to the oxygen source (100), and an output end of the first gas supply branch (106) is connected to the main gas supply pipeline (105);

a second gas supply branch (107), wherein an input end of the second gas supply branch (107) is connected to the anesthetic gas source (102), and an output end of the second gas supply branch (107) is connected to the main gas supply pipeline (105); and a third gas supply branch (108), wherein an input end of the third gas supply branch (108) is connected to the carbon dioxide source (103), and an output end of the third gas supply branch (108) is connected to the main gas supply pipeline (105).

4. The anesthesia ventilator device, as recited in claim 3, wherein the main gas supply pipeline (105) is sequentially connected with the air source (101), a first filter (1050), a first check valve (1051), a second check valve (1052), a third check valve (1053), a first pressure sensor (1054), and a first flow sensor (1055), and the output end of the main gas supply pipeline (105) is connected to the mask (104).

5. The anesthesia ventilator device, as recited in claim 4, wherein a heated humidifier (1056) is connected between the first flow sensor (1055) and the mask (104) on the main gas supply pipeline (105), and a breath gas generator (1057) is connected between the second check valve (1052) and the third check valve (1053).

6. The anesthesia ventilator device, as recited in claim 4, wherein the first gas supply branch (106) is sequentially connected to the oxygen source (100), a second filter (1060), a second pressure sensor (1061), a first flow control valve (1062), and a second flow sensor (1063); the output end of the first gas supply branch (106) is connected between the first filter (1050) and the first check valve (1051);

the second gas supply branch (107) is sequentially connected to the anesthetic gas source (102), a third filter (1070), a third pressure sensor (1071), a second flow control valve (1072), and a third flow sensor (1073); the output end of the second gas supply branch (107) is connected between the first check valve (1051) and the second check valve (1052); and the third gas supply branch (108) is sequentially connected to the carbon dioxide source (103), a fourth filter (1080), a fourth pressure sensor (1081), and a third flow control valve (1082); the output end of the third gas supply branch (108) is connected between the third check valve (1053) and the first pressure sensor (1054).

7. The anesthesia ventilator device, as recited in claim 4, wherein one end of the exhalation circuit (109) is connected to the first gas supply branch (106), and the other end is connected to the mask (104); in the direction from the first gas supply branch (106) to the mask (104), there are sequentially connected a fourth flow control valve (1090), a fifth pressure sensor (1091), and a pressure regulating diaphragm valve (1092);

an output end of the pressure regulating diaphragm valve (1092) is connected to the environment (1093);

an exhalation branch is connected between the fifth pressure sensor (1091) and the pressure regulating diaphragm valve (1092), and a throttle valve (1094) is provided on the exhalation branch; an output end of the throttle valve (1094) is connected to the environment (1093).

8. The anesthesia ventilator device, as recited in claim 1, wherein the anesthetic gas source (102) is any one of a nitrous oxide gas source, an ether gas source, a sevoflurane gas source, and a desflurane gas source.

9. The anesthesia ventilator device, as recited in claim 1, further comprising:

an exhalation circuit (109), wherein one end of the exhalation circuit (109) communicates with the mask (104), and the other end, away from the mask (104), communicates with the environment (1093); and an exhaled impurity filtration cleaning assembly (3), wherein the exhaled impurity filtration cleaning assembly (3) is arranged between the mask (104) and the environment (1093) on the exhalation circuit (109);

the exhaled impurity filtration cleaning assembly (3) comprises:

a recovery filter assembly casing (300) installed on the exhalation circuit (109);

two symmetrically arranged impurity filter meshes (3000), which are mounted inside the recovery filter assembly casing (300), with mounting holes (3003) provided on the impurity filter meshes (3000);

a filter mesh mounting drive (3001) installed in a first mounting cavity (3004), wherein a magnetic compression piston (3005) is slidably connected in the first mounting cavity (3004), and a first elastic element (3006) is fixedly connected between the working end of the magnetic compression piston (3005) and a bottom of the first mounting cavity (3004); a piezoelectric ceramic (3007) is fixedly connected to the bottom of the first mounting cavity (3004);

a filter mesh mounting executing component (3002), which is installed in a second mounting cavity (3008), wherein two symmetrically arranged sliding blocks (3009) are slidably connected inside the second mounting cavity (3008), and a second elastic element (302) is fixedly connected between the two sliding blocks (3009); one end of the two sliding blocks (3009), away from the second elastic element (302), is used to cooperate with the mounting holes (3003); an electromagnet (3020) is fixedly connected to an end of the two sliding blocks (3009) near the second elastic element (302), and the electromagnet (3020) is electrically connected to the piezoelectric ceramic (3007);

two symmetrically arranged cleaning liquid storage tanks (3021) containing cleaning liquid, with a water inlet funnel (3022) connected to the cleaning liquid storage tanks (3021); and a filter mesh cleaning assembly (301), which is installed in a third mounting cavity (3010), wherein the filter mesh cleaning assembly (301) comprises:

a threaded shaft (3011), which is rotatably connected inside the third mounting cavity (3010);

a threaded nut (3012), which is threadedly connected to the threaded shaft (3011);

a connecting bracket (3013), which is fixedly connected to the threaded nut (3012);

a water outlet barrel (3014), which is fixedly connected to one end of the connecting bracket (3013) away from the threaded nut (3012), with several water outlet holes (3015) on the water outlet barrel (3014);

two symmetrically arranged electric cleaning extensible brushes (3016), which are fixedly connected to both sides of the water outlet barrel (3014);

a compression airbag (3017), which is sleeved on the threaded shaft (3011), with a third elastic element (3018) inside the compression airbag (3017); wherein the compression airbag (3017) is connected to a suction tube (3024), with one end of the suction tube (3024), away from the compression airbag (3017), serving as an inlet and located inside each of the cleaning liquid storage tanks (3021); an outlet of the compression airbag (3017) is connected to the water outlet barrel (3014), and a one-way valve is provided inside the suction tube (3024);

two symmetrically arranged impurity collection holes (3019), which are set inside the recovery filter assembly casing (300) and located directly below the impurity filter meshes (3000); and two symmetrically arranged partitions (3023), which are slidably connected inside the recovery filter assembly casing (300).

* * * * *